US010828251B1

(12) United States Patent
Kaline

(10) Patent No.: US 10,828,251 B1
(45) Date of Patent: Nov. 10, 2020

(54) HOMEOPATHIC FORMULATIONS

(71) Applicant: BioLyte Laboratories, LLC, Grand Rapids, MI (US)

(72) Inventor: Daniel Kaline, Grand Rapids, MI (US)

(73) Assignee: Biolyte Laboratories, LLC, Grand Rapids, MI (US)

(*) Notice: Subject to any disclaimer, the term of this patent is extended or adjusted under 35 U.S.C. 154(b) by 0 days.

(21) Appl. No.: 15/699,789

(22) Filed: Sep. 8, 2017

Related U.S. Application Data

(60) Provisional application No. 62/446,370, filed on Jan. 14, 2017.

(51) Int. Cl.
| | |
|---|---|
| *A61K 36/28* | (2006.01) |
| *A61K 9/00* | (2006.01) |
| *A61K 36/00* | (2006.01) |
| *A61K 47/44* | (2017.01) |
| *A61K 47/32* | (2006.01) |
| *A61K 47/12* | (2006.01) |
| *A61K 47/02* | (2006.01) |

(52) U.S. Cl.
CPC ............ *A61K 9/0014* (2013.01); *A61K 36/00* (2013.01); *A61K 47/02* (2013.01); *A61K 47/12* (2013.01); *A61K 47/32* (2013.01); *A61K 47/44* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 5,006,338 A | 4/1991 | Luenemann | |
| 5,997,876 A | 12/1999 | Shikhashvili et al. | |
| 6,146,639 A | 11/2000 | Merich | |
| 6,447,788 B1 | 9/2002 | Strathausen | |
| 6,770,263 B1 | 8/2004 | Brucker | |
| 7,229,648 B2 | 6/2007 | Dreyer | |
| 7,351,739 B2 | 4/2008 | Ho et al. | |
| 7,781,429 B2 | 8/2010 | Schwarz et al. | |
| 7,871,647 B1 | 1/2011 | Paradise | |
| 7,923,040 B2 * | 4/2011 | Dreyer ............... | A61K 9/06 424/725 |
| 8,999,401 B2 * | 4/2015 | Luria ............... | A61K 8/02 424/401 |
| 9,545,429 B1 * | 1/2017 | Kaline ............... | A61K 36/00 |
| 2006/0165812 A1 * | 7/2006 | Charron ............... | A61K 33/00 424/600 |
| 2007/0134299 A1 | 6/2007 | Giles | |
| 2007/0212434 A1 | 9/2007 | Day et al. | |
| 2008/0038219 A1 | 2/2008 | Mosbaugh et al. | |
| 2008/0145454 A1 | 6/2008 | Wycoff | |
| 2009/0232904 A1 | 9/2009 | Quinto et al. | |
| 2010/0316737 A1 | 12/2010 | Farrington et al. | |
| 2011/0038949 A1 | 2/2011 | Oswal et al. | |
| 2013/0236606 A1 * | 9/2013 | Duoibes ............... | A61K 8/44 426/74 |

FOREIGN PATENT DOCUMENTS

| | | |
|---|---|---|
| DE | 3316726 | 11/1984 |
| FR | 2255887 | 7/1975 |
| GB | 2311009 | 9/1997 |
| RU | 2190419 | 10/2002 |

OTHER PUBLICATIONS

Martin J. Therapeutic Potential of KELEA Activated Water. International J of Complementary & Alternative Medicine 1(1)Feb. 1-4, 2015. (Year: 2015).*
Tahir A. et al. Determining the Minimum Inhibitory Concentration of Fulvic Acid on Early S. mutans Biofilm Formation. ScholarWorks IUPUI 2014. (Year: 2014).*
Berrebi et al., Treatment of pain due to unwanted lactation with a homeopathic preparation given in the immediate post-partum period, 30 J Gynecol Obstet Biol Reprod (Paris) 353-57 (2001) (English Abstract Provided).
Canadian Intellectual Property Office, dated Nov. 4, 2011 Search Report for App. No. 2518965.
Cordova et al., Protective properties of butanolic extract of the *Calendula officinalis* L. (marigold) against lipid peroxidation of rat liver microsomes and action as free radical scavenger, 7 Redox Rep 95-102 (2002).
Dr. Frank's Joint & Muscle Pain Relief product information, retrieved from https://www.drfrankspainrelief.com/formula.php on Aug. 19, 2011.
USPTO, Jun. 9, 2005 Examiner-Initiated Interview Summary for Application No. 10797009.
GMI's PainMed product information, retrieved from http://gmipainmed.com/PAIN_MED_ACTIVE_INGREDIENTS.html on Aug. 19, 2011.
USPTO, Sep. 24, 2004 PCT International Search Report for PCT/US04/05231.

(Continued)

*Primary Examiner* — Ralph J Gitomer
(74) *Attorney, Agent, or Firm* — Adam R. Stephenson, Ltd.

(57) ABSTRACT

Implementations of topical homeopathic compositions may include: an actives portion including a plurality of active ingredients and a base including a plurality of inactive ingredients, wherein the plurality of active ingredients include: one of tincture and homeopathic preparations of *Antimonium crudum, Arnica montana, Arsenicum album, Atropa belladonna, Camphora officinalis, Carbolicum acidum, Cicuta virosa, Cimicifuga racemosa, Cina, Cinchona officinalis*-China, *Cocculus indicus, Codeinum, Colocynthis, Crocus sativus, Cuprum metallicum, Eupionum, Gelsemium sempervirens, Gnaphalium polycephalum, Hyoscyamus niger, Hypericum perforatum, Ignatia amara, Ipecacuanha, Jatropha curcas, Kali bromatum, Kali carbonicum, Kathyrus sativus, Lactuca virosa, Loleum temulentum, Lycopodium clavatum, Magnesium phosphoricum, Physostigma venenosum, Pinus sylvestris, Pulsatilla pratensis, Rhamnus californica, Ruta graveolens, Scutellaria lateriflora, Stramonim, Strychninum purum, Sulfonalum, Taraxacum officinale, Thuja occidentalis, Ustilago maydis, Valeriana officinalis, Veratrum album, Zincum metallicum, Zincum valerianicum, Zizia aurea*, and any combination thereof.

4 Claims, No Drawings

(56) References Cited

OTHER PUBLICATIONS

EPICURE product label. Available at least as early as 2016.
Friese et al., The homeopathic treatment of otitis media in children—comparisons with conventional therapy, 35 International Journal of Clinical Pharmacology and Therapeutics 296-301 (1997) (last page missing).
HomeopathyHome.com web pages, retrieved through web.archive.org website. Available at least as early as 2001.
911 Stress Control product information website, retrieved through web.archive.org website. Available at least as early as Feb. 23, 2002.
USPTO, Jun. 21, 2005 Office Action (Non-Final Rejection) of App. No. 10797009.
Knuesel et al., Arnica montana gel in osteoarthritis of the knee: an open, multicenter clinical trial, 19 Adv Ther 209-18 (2002).
Kumar et al, Anti-inflammatory and analgesic activity of Indian *Hypericum perforatum* L., 39 Indian J Exp Biol 339-43 (2001).
Painazol product information, retrieved from http://www.painazol.com/?ssid=0e1d611447ad692e7c278fc08a2026b0 on Aug. 19, 2011.
Rhumatol product information, retrieved from http://www.rhumatol.com/?ssid=0e1d611447ad692e7c278fc08a2026b0 on Aug. 19, 2011.
Traumeel product label. Available at least as early as 2016.
van Haselen et al., A randomized controlled trial comparing topical piroxicam gel with a homeopathic gel in osteoarthritis of the knee, 39 Rheumatology 714-19 (2000).
Painazol Pain Relief Marketing Information (marketing start date: May 20, 2010).
Trace Mineral Reviews, available at www.trace-mineral-drops.com. Available at least as early as Jan. 6, 2014.

\* cited by examiner

HOMEOPATHIC FORMULATIONS

CROSS REFERENCE TO RELATED APPLICATIONS

This document claims the benefit of the filing date of U.S. Provisional Patent Application 62/446,370, entitled "Homeopathic Formulations" to Daniel Kaline which was filed on Jan. 14, 2017, the disclosure of which is hereby incorporated entirely herein by reference.

BACKGROUND

1. Technical Field

Aspects of this document relate generally to compositions used in homeopathic treatment of symptoms, diseases, and injuries

2. Background

A large number of plant and animal extracts and chemicals have been observed to, in diluted quantities, enable healing and reduction of symptoms associated with diseases and injuries of the (human or animal) body. Homeopathic compositions operate using diluted concentrations of substances that modify the frequency of the diluent and have been observed to produce a corresponding response within the body when applied externally or taken internally.

SUMMARY

Implementations of topical homeopathic compositions may include: an actives portion including a plurality of active ingredients and a base including a plurality of inactive ingredients, wherein the plurality of active ingredients include: one of tincture and homeopathic preparations of *Antimonium crudum, Arnica montana, Arsenicum album, Atropa belladonna, Camphora officinalis, Carbolicum acidum, Cicuta virosa, Cimicifuga racemosa, Cina, Cinchona officinalis*-China, *Cocculus indicus, Codeinum, Colocynthis, Crocus sativus, Cuprum metallicum, Eupionum, Gelsemium sempervirens, Gnaphalium polycephalum, Hyoscyamus niger, Hypericum perforatum, Ignatia amara, Ipecacuanha, Jatropha curcas, Kali bromatum, Kali carbonicum, Kathyrus Sativus, Lactuca virosa, Loleum temulentum, Lycopodium clavatum, Magnesium phosphoricum, Physostigma venenosum, Pinus sylvestris, Pulsatilla pratensis, Rhamnus californica, Ruta graveolens, Scutellaria lateriflora, Stramonim, Strychninum purum, Sulfonalum, Taraxacum officinale, Thuja occidentalis, Ustilago maydis, Valeriana officinalis, Veratrum album, Zincum metallicum, Zincum valerianicum, Zizia aurea,* and any combination thereof.

Implementations of topical homeopathic compositions may include one, all, or any of the following:

The base may include acrylates/C-10-30 alkyl acrylate cross-polymer, colloidal silver, potassium sorbate, citric acid, fulvic acid, water, sodium hydroxide, vegetable glycerin, and any combination thereof.

The base may be a gel base and includes acrylates/C-10-30 alkyl acrylate cross-polymer, vegetable glycerin, colloidal silver, citric acid, fulvic liquid minerals, potassium sorbate, water, and sodium hydroxide.

The fulvic acid may include a fulvic liquid mineral composition having 73 trace minerals.

The actives portion may include 50% to 90% by weight of the total formulation and the inactives portion may include 10%-50% by weight of the total formulation.

Implementations of topic homeopathic formulations may include an 18% sodium hydroxide solution.

Implementations of topical homeopathic compositions may include: an actives portion including a plurality of active ingredients and a base including a plurality of inactive ingredients. The plurality of active ingredients may include: one of tinctures and homeopathic preparations of *Antimonium crudum, Arnica montana, Arsenicum album, Atropa belladonna, Camphora officinalis, Carbolicum acidum, Cicuta virosa, Cimicifuga racemosa, Cina, Cinchona officinalis*-China, *Cocculus indicus, Codeinum, Colocynthis, Crocus sativus, Cuprum metallicum, Eupionum, Gelsemium sempervirens, Gnaphalium polycephalum, Hyoscyamus niger, Hypericum perforatum, Ignatia amara, Ipecacuanha, Jatropha curcas, Kali bromatum, Kali carbonicum, Kathyrus sativus, Lactuca virosa, Loleum temulentum, Lycopodium clavatum, Magnesium phosphoricum, Physostigma venenosum, Pinus sylvestris, Pulsatilla pratensis, Rhamnus californica, Ruta graveolens, Scutellaria lateriflora, Stramonim, Strychninum purum, Sulfonalum, Taraxacum officinale, Thuja occidentalis, Ustilago maydis, Valeriana officinalis, Veratrum album, Zincum metallicum, Zincum valerianicum, Zizia aurea,* and any combination thereof. The plurality of inactive ingredients may include: acrylates/C-10-30 alkyl acrylate cross-polymer, colloidal silver, potassium sorbate, citric acid, fulvic acid, water, sodium hydroxide, vegetable glycerin, and any combination thereof.

Implementations of topical homeopathic compositions may include one, all, or any of the following:

The base may be a gel base and the gel base may include: acrylates/C-10-30 alkyl acrylate cross-polymer, vegetable glycerin, colloidal silver, citric acid, fulvic liquid minerals, potassium sorbate, water, and sodium hydroxide.

The fulvic acid may include a fulvic liquid mineral composition comprising 73 trace minerals.

Implementations of topic homeopathic formulations may include an 18% sodium hydroxide solution.

Implementations of topical homeopathic compositions may include: an actives portion comprising a plurality of active ingredients and a base comprising a plurality of inactive ingredients. The plurality of active ingredients may include: one of tinctures and homeopathic preparations of *Antimonium crudum, Arnica montana, Arsenicum album, Atropa belladonna, Camphora officinalis, Carbolicum acidum, Cicuta virosa, Cimicifuga racemosa, Cina, Cinchona officinalis*-China, *Cocculus indicus, Codeinum, Colocynthis, Crocus sativus, Cuprum metallicum, Eupionum, Gelsemium sempervirens, Gnaphalium polycephalum, Hyoscyamus niger, Hypericum perforatum, Ignatia amara, Ipecacuanha, Jatropha curcas, Kali bromatum, Kali carbonicum, Kathyrus Sativus, Lactuca virosa, Loleum temulentum, Lycopodium clavatum, Magnesium phosphoricum, Physostigma venenosum, Pinus sylvestris, Pulsatilla pratensis, Rhamnus californica, Ruta graveolens, Scutellaria lateriflora, Stramonim, Strychninum purum, Sulfonalum, Taraxacum officinale, Thuja occidentalis, Ustilago maydis, Valeriana officinalis, Veratrum album, Zincum metallicum, Zincum valerianicum, Zizia aurea,* and any combination thereof. The base may be a gel base and may include: acrylates/C-10-30 alkyl acrylate cross-polymer, vegetable glycerin, colloidal silver, citric acid, fulvic liquid minerals, potassium sorbate, water, and sodium hydroxide.

Implementations of topical homeopathic compositions may include one, all, or any of the following:

The base may further include one of: acrylates/C-10-30 alkyl acrylate cross-polymer, colloidal silver, potassium sorbate, citric acid, fulvic acid, water, sodium hydroxide, and vegetable glycerin.

The fulvic acid may include a fulvic liquid mineral compositions including 73 trace minerals.

The active portions may include 50% to 90% by weight of the total formulation and the inactives portion may include 10% to 50% by weight of the total formulation.

Implementations of topical homeopathic compositions may include an 18% sodium hydroxide solution.

The foregoing and other aspects, features, and advantages will be apparent to those artisans of ordinary skill in the art from the DESCRIPTION and DRAWINGS, and from the CLAIMS.

DESCRIPTION

This disclosure, its aspects and implementations, are not limited to the specific components, assembly procedures or method elements disclosed herein. Many additional components, assembly procedures and/or method elements known in the art consistent with the topical homeopathic compositions will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such topical homeopathic compositions and implementing components and methods, consistent with the intended operation and methods.

Implementations of homeopathic compositions in this document relate specifically to ameliorating the symptoms associated with Restless Leg Syndrome (RLS). Symptoms of RLS may include the uncontrollable need to move legs, including but not limited to, symptoms at night. The homeopathic formulas disclosed herein may also be used to relieve muscle cramps (knots), any muscle twitching and generally calming muscles.

Dr. Samuel Hahnemann (1755-1843), a German physician considered by many to be the father of Homeopathy, believed that human beings have a capacity for healing themselves and that the symptoms of disease reflect the individual's struggle to overcome their illness. He discovered the principle that, what a particular substance could cause in the way of symptoms, could also cure. Based on this understanding, Hahnemann proposed the "Law of Similars." In other words, if someone has certain symptoms, then regardless of the disease involved, taking a medicine that causing the same symptoms but highly diluted would produce opposite symptoms. In homeopathic medicine, this later became known as the "Law of Infinitesimals." Homeopathic medicines and substances are considered by homeopaths to act as remedies by creating Informational Energy, stimulating the internal vital force of the body, and thereby initiating an immune and healing response within the body to heal itself. In practice, while little or no adverse side effects may be observed because of the dilution, a strong positive effect can be seen as homeopaths believe the solutions works with the body at sub-atomic frequencies. Homeopathic compositions have been described as being effective by delivering a small amount of a substance that, in large quantities, would create the symptom being observed, thereby allowing the body to properly develop a response that ultimately is able to eliminate the cause of the symptom being observed. A wide variety of conditions may be treated using homeopathic compositions, including but not limited to general pain, inflammation, joint pain, muscle restlessness and twitching, as well as many other symptoms.

Homeopathy operates on a different principle than conventional over-the-counter preparations. Those solutions that are most concentrated in a particular component are considered least potent, while those that are least concentrated (highly diluted) in a particular component are most potent. Based on the general principle of treating like with like, homeopathic preparations work using components that in large doses would create symptoms like those the patient is currently experiencing. However, by deliberately applying sequentially highly diluted or "potentized" preparations of these same components through a process called "succussion," the patient's body may be stimulated to take the actions needed to eliminate the symptoms associated with the disease and help facilitate the healing needed to recover from an injury. Each component of a homeopathic mixture may be made from a plant, chemical compound, or animal in the form of a tincture at a specified concentration or ratio of ethyl alcohol. The tincture is then sequentially diluted or succussed to a desired dilution to form a homeopathic preparation. Homeopathic ingredients that have been highly diluted are also referred to as high potency. Ultra high dilutions that may be used could produce solutions in which it may be close to physically impossible for a single molecule from the original component to be present in the solution applied. Homeopaths may refer to the process of succussing a tincture as establishing the frequency of the solution and using the resulting frequency of the solution to work with the body to provoke a healing response.

Implementations of topical homeopathic compositions like those disclosed herein may include an actives portion including a plurality of active ingredients and a base including a plurality of inactive ingredients. In the various implementations, the plurality of active ingredients include tinctures and/or homeopathic preparations of various combinations of *Antimonium crudum* (Black sulphide of Antimony), *Arnica montana* (Leopard's Bane), *Arsenicum album* (Arsenious Acid, Arsenic Trioxide), *Atropa belladonna* (Deadly Nightshade), *Camphora officinalis* (Camphor), *Carbolicum acidum* (Phenol, Carbolic Acid), *Cicuta virosa* (Water Hemlock), *Causticum* (Hahnemann's distillation of Potassium Bisulfate), *Cimicifuga racemosa* (Black Snakeroot), *Cina* (Wormseed), *Cinchona officinalis*-China (Peruvian Bark), *Cocculus indicus* (Indian Cockle), *Codeinum* (An Alkaloid from Opium), *Colocynthis* (Bitter Cucumber), *Crocus sativus* (Saffron), *Cuprum metallicum* (Copper), *Eupionum* (Wood Tar Distillation), *Gelsemium sempervirens* (Yellow Jasmine), *Gnaphalium polycephalum* (Cud-weed, Old Balsam), *Hyoscyamus niger* (Henbane), *Hypericum perforatum* (St. John's Wort), *Ignatia amara* (St. Ignatius Bean), *Ipecacuanha* (Ipecac Root), *Jatropha curcas* (Purging Nut), *Kali bromatum* (Potassium Bromide), *Kali carbonicum* (Potassium Carbonate), *Kathyrus Sativus* (Chick-Pea), *Lactuca virosa* (Acrid Lettuce), *Loleum temulentum* (Darnel), *Lycopodium clavatum* (Club Moss), *Magnesium phosphoricum* (Phosphate of Magnesia), *Physostigma venenosum* (Calabar Bean), *Pinus sylvestris* (scotch Pine), *Pulsatilla pratensis* (Wild flower), *Rhamnus californica* (California Coffee Tree), *Ruta graveolens* (Rue Bitterwort), *Scutellaria lateriflora* (Skullcap), *Stramonim* (Thorn-Apple), *Strychninum purum* (Alkaloid of Nux Vomica), *Sulfonalum* (A Coal Tar Product), *Taraxacum officinale* (Dandelion), *Thuja occidentalis* (Arbor Vitae), *Ustilago Maydis* (Corn-smut), *Valeriana officinalis* (Valerian), *Ver-*

*atrum album* (American White Hellebore), *Zincum metallicum* (Zinc), *Zincum valerianicum, Zizia aurea* (Thaspium Aureum, Medow Parsnip), or any combination thereof.

Implementations of topical homeopathic formulations discussed herein are disclosed for the purpose of relieving the symptoms associated with Restless Leg Syndrome and including but not limited to relieving some cramping and twitching of such muscle caused by not but not limited to RLS alone.

The inactives portion of the topical homeopathic formations disclosed herein may be included in a gel base. The inactives portion in various implementations may include acrylates/C-10-30 alkyl acrylate cross-polymer, colloidal silver, potassium sorbate (natural preservative), citric acid (natural preservative), fulvic liquid minerals (used to amplify the homeopathic actives sub-atomic resonance), water, sodium hydroxide (used as a neutralizer for the polymer), and/or vegetable glycerin (USP, used as a mild moisturizer). Where the inactives portion is included in a gel base, it may also include acrylates/C-10-30 alkyl acrylate cross-polymer, vegetable glycerin, colloidal silver, citric acid, fulvic liquid minerals, potassium sorbate, water, and sodium hydroxide. Inactive ingredients in various homeopathic formulations may be any disclosed in U.S. patent application Ser. No. 13/225,429 to Daniel Kaline, entitled "Homeopathic Formulations," filed Sep. 3, 2011, now U.S. Pat. No. 9,545,429 (the '429 patent), the disclosure of which is incorporated entirely herein by reference.

The fulvic liquid minerals included in implementations of bases disclosed in this document may be any of various compositions extracted from fulvic mineral bases. In particular implementations, the fulvic liquid mineral composition may include 73 trace minerals extracted using a supplier's proprietary process that performs the extraction from a fulvic acid containing mineral base resulting in a liquid that is slightly alkaline rather than acidic. Without being bound by any theory, the inclusion of the fulvic liquid minerals acts to further potentiate the activity of the various homeopathic preparations included as active ingredients in the actives portion, although the fulvic liquid minerals are listed in the inactives portion. Examples of fulvic liquid minerals that may be used in various homeopathic formulations disclosed herein may be found in Appendix A, the disclosure of which is hereby incorporated entirely herein by reference.

In implementations of the base, the same fulvic liquid minerals and colloidal silver may be utilized as were disclosed in the topical gel implementation. The fulvic liquid minerals may be processed through a reverse osmosis restructured water filter as part of the process of preparation. The effect of the fulvic liquid minerals may also be the same on the potentiation of the active ingredients as it was discussed with the topical gel implementation.

Implementations of formulations may include water. In various implementations, the water may be purified vortexed alkaline water. In other implementations, the water may be structured water. Any of the water types disclosed in the '429 patent may be used in various implementations.

Various implementations may include actives portions of about 50%-90% by weight of the total formulation and base/inactives portions of about 10%-50% by weight of the total formulation. The acrylates/C-10-30 alkyl acrylate cross-polymer [the International Nomenclature Cosmetic Ingredient (INCI) name] is a polymer gel designed to contain extremely low levels of benzene-containing residual solvent, in the range of 0.5 ppm. Such a polymer gel may exhibit rapid wetting properties not requiring agitation, high thickening efficiency, limited electrolyte tolerance, excellent clarity in applications, and superior aesthetic performance, depending upon the implementation selected. Implementations of such a polymer gel are marketed under the trade name CARBOPOL® Ultrez 10 NF Polymer by Lubrizol Advanced Materials of Cleveland, Ohio. Many conventional polymer gels are specified to contain 1000 ppm of residual benzene, which while within the limits set by the current edition of the United States Pharmacopoeia/National Formulary (USP/NF) for topical use, has been judged to be too high in many European countries, where the use of these polymer gels have been banned.

In various implementations, the use of sodium hydroxide (NaOH) in an 18% solution is used as a neutralizing agent. The NaOH may act to buffer the gel base and to enable thickening of the polymer gel. This is in contrast with many conventional gels which utilize triethanolamine. Triethanolamine contains amines which are subjects of concern in the alternative health care industry in the U.S. and Europe. A colloidal silver solution may be utilized as an anti-microbial agent only in the base. In particular implementations, the colloidal silver solution may avoid the toxicity issues related to the use of conventional colloidal silver products by selecting structured silver solutions with particles of silver that are very small in size compared with conventional silver products. The use of the structured silver is in contrast with conventional gels, which utilize methylparaben and other parabens to act as preservatives and anti-microbial agents.

The potency of any one of the plurality of active ingredients included in the actives portion may be between tincture to about 100×, between 1C to about 30C, or LM-1 to about LM-3.

Several different dilution scales are used in homeopathy to describe the end concentration of a given homeopathic preparation for a particular component. The centesimal or C scale is based on diluting by a factor of 100 at each stage. For example, to create a 1C solution, 99 drops of diluent would be added to 1 drop of a tincture of the component. To create a 2C solution, 99 drops of diluent would be added to 1 drop of a 1C solution of the component. The decimal or D scale is based on diluting by a factor of 10 at each stage, or by adding 9 drops of diluent to 1 drop of tincture to create a 1× or 1D solution. A 100× solution would be created by starting with a 1× solution and then repeating the process of taking one drop of the last dilution and adding 9 more drops of diluents to it 9 additional times. This type of dilution is base 10 logarithmic in scale. The quintamillesimal (Q) or LM scale is the process of creating a dilution of 1:50,000 in the first dilution. Accordingly, an LM-1 homeopathic preparation is prepared by sequentially succussing one drop of tincture with 49,999 drops of diluent. In practice, homeopathic preparations of given components range in dilution from tincture to 400× on the Decimal scale, tincture to 200C on the C scale, and LM-1 to LM-3 on the LM scale.

The observed effectiveness of a given homeopathic preparation can depend upon the method used to administer it to the patient. For example, lower potency (higher concentration) homeopathic ingredients appear to have better results when used as a topical treatment application when compared to high potency ingredients. In contrast, high potency homeopathic ingredients work well when administered orally or internally. A potential problem with administering lower potency homeopathic preparations such as tinctures, 1×, 2×, 3× and 4× dilutions topically is that homeopathic ingredients are cut with ethyl alcohol as a preservative during the preparation process and to produce the mother tinctures for further dilution during the process of increasing potency. As a result, tinctures and 1× potencies can contain between about 30% to about 60% ethyl alcohol. This high concentration of ethanol may be necessary to prevent bacterial growth while still retaining the benefit of the active ingredient. Low potency ingredients may work well when the benefit of the ingredient is not necessarily being used in the homeopathic capacity of like curing like, but is also being used like a conventional allopathic medicine. However, if a homeopathic ingredient is used in lower potency where the application of the homeopathic ingredient is intended to operate homeopathically based on the principle of like curing like, then low potency application of those ingredients could pose a potential health risk to the skin due to the high concentration of the particular component in what is being applied to the skin.

Low potency ingredients may also present challenges when compared to high potency mixtures in that they tend to be less stable and characteristically have a much shorter shelf life. High potency ingredients, due to the very low concentration of ethanol and/or high amount of purified water diluent, tend to perform better in terms of stability and longer shelf life. Another challenge from the homeopath's perspective with low potency homeopathic preparations is that although they may perform well topically, they may also lack the ability to affect tissues deeper in the body. When a solution is prepared for the purpose of homeopathic topical application, a strategy is to blend in both low and high potency ingredients together (i.e., include both a 1× preparation and a 20× preparation of the same component in the same product) to provide a dual benefit. This may not be as safe when strictly using higher potency ingredients, however, when the solution is to be administered to younger people who will be more sensitive to the effects of the lower potency ingredients, unless the monograph calls for tincture external use, these low dilutions can provide a benefit for a particular ingredient. Such monographed ingredients can provide a benefit for both low and high dilutions.

The various components included in implementations of homeopathic preparations disclosed in this document are selected from those officially listed in the *Homeopathic Pharmacopoeia of the United States* (HPUS). A description of the specific symptoms each of the components disclosed in this document may work to remedy may be found in William Boericke, M. D., *Materia Medial*, 9th Edition (1927), the relevant disclosures of which for each component are hereby incorporated herein by reference.

Table 1 is lists a set of all active ingredients (components) that may be used in the various preparation implementations disclosed in this document along with the range of dilutions that may be utilized for each ingredient. In Table 1, tincture refers to the mother tincture as defined in the HPUS.

TABLE 1

| Active Ingredients | |
| --- | --- |
| Component | Dilution Range |
| Antimonium Crudum | Tinct.-100X, 1C-30C, LM-1 to LM-3 |
| *Arnica montana* | Tinct.-100X, 1C-30C, LM-1 to LM-3 |
| Arsenicum Album | Tinct.-100X, 1C-30C, LM-1 to LM-3 |
| *Atropa Belladonna* | Tinct.-100X, 1C-30C, LM-1 to LM-3 |
| Camphora Officinalis | Tinct.-100X, 1C-30C, LM-1 to LM-3 |
| Carbolicum Acidum | Tinct.-100X, 1C-30C, LM-1 to LM-3 |
| Cicuta Virosa | Tinct.-100X, 1C-30C, LM-1 to LM-3 |
| Causticum | Tinct.-100X, 1C-30C, LM-1 to LM-3 |
| *Cimicifuga racemosa* | Tinct.-100X, 1C-30C, LM-1 to LM-3 |
| Cina | Tinct.-100X, 1C-30C, LM-1 to LM-3 |

TABLE 1-continued

| Active Ingredients | |
| --- | --- |
| Component | Dilution Range |
| Cinchona Officinalis-China | Tinct.-100X, 1C-30C, LM-1 to LM-3 |
| Cocculus Indicus | Tinct.-100X, 1C-30C, LM-1 to LM-3 |
| Codeinum | Tinct.-100X, 1C-30C, LM-1 to LM-3 |
| Colocynthis | Tinct.-100X, 1C-30C, LM-1 to LM-3 |
| Crocus Sativus | Tinct.-100X, 1C-30C, LM-1 to LM-3 |
| Cuprum Metallicum | Tinct.-100X, 1C-30C, LM-1 to LM-3 |
| Eupionum | Tinct.-100X, 1C-30C, LM-1 to LM-3 |
| Gelsemium Sempervirens | Tinct.-100X, 1C-30C, LM-1 to LM-3 |
| *Gnaphalium polycephalum* | Tinct.-100X, 1C-30C, LM-1 to LM-3 |
| *Hypericum perforatum* | Tinct.-100X, 1C-30C, LM-1 to LM-3 |
| Hyoscyamus Niger | Tinct.-100X, 1C-30C, LM-1 to LM-3 |
| *Ignatia Amara* | Tinct.-100X, 1C-30C, LM-1 to LM-3 |
| Ipecacuanha | Tinct.-100X, 1C-30C, LM-1 to LM-3 |
| *Jatropha curcas* | Tinct.-100X, 1C-30C, LM-1 to LM-3 |
| Kali bromatum | Tinct.-100X, 1C-30C, LM-1 to LM-3 |
| Kali carbonicum | Tinct.-100X, 1C-30C, LM-1 to LM-3 |
| Kathyrus Sativus | Tinct.-100X, 1C-30C, LM-1 to LM-3 |
| Lactuca Virosa | Tinct.-100X, 1C-30C, LM-1 to LM-3 |
| Loleum Temulentum | Tinct.-100X, 1C-30C, LM-1 to LM-3 |
| *Lycopodium clavatum* | Tinct.-100X, 1C-30C, LM-1 to LM-3 |
| Magnesium Phosphoricum | Tinct.-100X, 1C-30C, LM-1 to LM-3 |
| Physostigma Venenosum | Tinct.-100X, 1C-30C, LM-1 to LM-3 |
| Pinus Sylvestris | Tinct.-100X, 1C-30C, LM-1 to LM-3 |
| Pulsatilla Pratensis | Tinct.-100X, 1C-30C, LM-1 to LM-3 |
| *Rhamnus californica* | Tinct.-100X, 1C-30C, LM-1 to LM-3 |
| *Ruta graveolens* | Tinct.-100X, 1C-30C, LM-1 to LM-3 |
| *Scutellaria lateriflora* | Tinct.-100X, 1C-30C, LM-1 to LM-3 |
| Stramonim | Tinct.-100X, 1C-30C, LM-1 to LM-3 |
| Strychninum Purum | Tinct.-100X, 1C-30C, LM-1 to LM-3 |
| Sulfonalum | Tinct.-100X, 1C-30C, LM-1 to LM-3 |
| *Taraxacum officinale* | Tinct.-100X, 1C-30C, LM-1 to LM-3 |
| Thuja Occidentalis | Tinct.-100X, 1C-30C, LM-1 to LM-3 |
| Ustilago Maydis | Tinct.-100X, 1C-30C, LM-1 to LM-3 |
| *Valeriana officinalis* | Tinct.-100X, 1C-30C, LM-1 to LM-3 |
| *Veratrum album* | Tinct.-100X, 1C-30C, LM-1 to LM-3 |
| Zincum Metallicum | Tinct.-100X, 1C-30C, LM-1 to LM-3 |
| Zincum Valerianicum | Tinct.-100X, 1C-30C, LM-1 to LM-3 |
| Zizia Aurea | Tinct.-100X, 1C-30C, LM-1 to LM-3 |

Table 2 includes Example 1 which is a combination of ingredients that may be combined to form an implementation of a topical homeopathic formulation for the treatment of RLS. The ingredients may be combined using the regular methods known in the art for homeopathic formulations.

TABLE 2

| Active Ingredients | |
| --- | --- |
| Component | Dilution Range |
| *Arnica montana* | Tinct.-100X, 1C-30C, LM-1 to LM-3 |
| Belladonna | Tinct.-100X, 1C-30C, LM-1 to LM-3 |
| Causticum | Tinct.-100X, 1C-30C, LM-1 to LM-3 |
| *Cimicifuga racemosa* | Tinct.-100X, 1C-30C, LM-1 to LM-3 |
| Cina | Tinct.-100X, 1C-30C, LM-1 to LM-3 |
| *Gnaphalium polycephalum* | Tinct.-100X, 1C-30C, LM-1 to LM-3 |
| *Hypericum perforatum* | Tinct.-100X, 1C-30C, LM-1 to LM-3 |
| *Ignatia Amara* | Tinct.-100X, 1C-30C, LM-1 to LM-3 |
| *Jatropha curcas* | Tinct.-100X, 1C-30C, LM-1 to LM-3 |
| Kali Bromatum | Tinct.-100X, 1C-30C, LM-1 to LM-3 |
| Kali carbonicum | Tinct.-100X, 1C-30C, LM-1 to LM-3 |
| *Lycopodium clavatum* | Tinct.-100X, 1C-30C, LM-1 to LM-3 |
| *Rhamnus californica* | Tinct.-100X, 1C-30C, LM-1 to LM-3 |
| *Ruta graveolens* | Tinct.-100X, 1C-30C, LM-1 to LM-3 |
| *Scutellaria lateriflora* | Tinct.-100X, 1C-30C, LM-1 to LM-3 |
| *Taraxacum officinale* | Tinct.-100X, 1C-30C, LM-1 to LM-3 |
| *Valeriana officinalis* | Tinct.-100X, 1C-30C, LM-1 to LM-3 |
| *Veratrum album* | Tinct.-100X, 1C-30C, LM-1 to LM-3 |

A wide variety of combinations of potential active ingredients at desired potencies are possible using the list of ingredients and dilutions listed in Table 1. For example, the same number of active ingredients may be included in one preparation at a particular set of potencies, while in another implementation, the active ingredients may be used at a different set of potencies. Table 2 is an example of such an implementation that includes less that the full number in Table 1. The examples provided of each implementation are for the exemplary purposes of this disclosure. Those of ordinary skill in the art will readily be able to create additional implementations using the principles disclosed herein.

In various implementations, the actives portion of the gel may constitute about 50-90% of the total weight of the gel. In various implementations, the base/inactives portion may be about 10-50% of the total weight of the topical gel.

While the use of specific inactive ingredients is described above and in other descriptions of base implementations disclosed in this document, these disclosures are for the exemplary purposes of this disclosure only. Accordingly, base implementations that may be utilized may include, one, all, or any of the various inactive ingredients disclosed in this document in any desired ratio in order to produce, by non-limiting example, a desired viscosity, a desired dry time on the skin, a desired taste, a desired shelf life, a desired biological activity, a desired potentiation of the homeopathic activity of the active ingredients, or any other desired characteristic or property of a gel homeopathic preparation. In particular implementations, ethanol may be added to the base of topical gel implementations in weight percentages between about 0.2% to about 10% to aid in enhancing the drying of the gel on the surface of the skin after application and/or to achieve a desired viscosity of the gel at the time of application. A wide variety of base implementations may be constructed using the principles disclosed in this document.

In various implementations, the topical homeopathic preparation may be prepared by blending together the actives portion and the base portion, with about 50-90% of the weight of the final preparation coming from the actives portion and about 10-90% of the weight of the final preparation coming from the inactive ingredients in the base in particular implementations.

In various implementations, the final composition may be packaged in an airless pump bottle configured to aid in dispensing by those suffering from limited dexterity and/or painful mobility. The pump bottle may have a volume of 50 mL (56.7 mL in particular implementations). Such airless pump bottles may be designed to be incapable of aspirating the gel back into the tube because of an internal piston which, when depressed, is configured to eliminate the likelihood of the introduction of any contamination into the preparation. The blending and packaging processes may be performed in a FDA approved facility with a current Good Manufacturing Practices (cGMP) rating.

The topical gel preparation may be used by adults and children 2 years of age or older. To use, the patient may gently apply a thin layer of the gel sufficient to cover the entire affected area. This may take place immediately at the onset of Restless Leg Syndrome symptoms. Users may use as needed. In specific implementations, the dosing may be limited to no more than 6 applications daily.

In places where the description above refers to particular implementations of topical homeopathic compositions and implementing components, sub-components, methods and sub-methods, it should be readily apparent that a number of modifications may be made without departing from the spirit thereof and that these implementations, implementing components, sub-components, methods and sub-methods may be applied to other topical homeopathic compositions.

What is claimed is:

1. A topical homeopathic formulation comprising an actives portion comprising a plurality of active ingredients and a base comprising a plurality of inactive ingredients, wherein the plurality of active ingredients consist essentially of:

homeopathic preparations of *Arnica montana* 4X, *Atropa belladonna* 4X, *Causticum* 4X *Cimicifuga racemosa* 4X, *Cina* 8X, *Gnaphalium polycephalum* 4X, *Hypericum perforatum* 4X, *Ignatia amara* 4X, *Jatropha curcas* 8X, *Kali bromatum* 4X, *Kali carbonicum* 4X, *Lycopodium clavatum* 4X, *Rhamnus californica* 4X, *Ruta graveolens* 4X, *Scutellaria lateriflora* 4X, *Taraxacum officinale* 4X, *Valeriana officinalis* 4X, *Veratrum album* 8X ; and wherein the base is a gel base comprising:

acrylates/C-10-30 alkyl acrylate cross-polymer, vegetable glycerin, colloidal silver, citric acid, fulvic liquid minerals, potassium sorbate, water, and sodium hydroxide.

2. The formulation of claim 1, wherein the fulvic acid comprises a fulvic liquid mineral composition comprising 73 trace minerals.

3. The formulation of claim 1, wherein the actives portion comprises 50% to 90% by weight of the total formulation and the inactives portion comprises 10%-50% by weight of the total formulation.

4. The formulation of claim 1, further comprising a sodium hydroxide solution having a concentration of 18%.

* * * * *